(12) United States Patent
Mohamed Ibrahim

(10) Patent No.: US 12,674,163 B2
(45) Date of Patent: Jul. 7, 2026

(54) COMB SHAPED ANTIVIRALS ENDING WITH OR WITHOUT CHAIN TERMINATING BASES

(71) Applicant: Ahmed Ibrahim Mohamed Ibrahim, Khartoum (SD)

(72) Inventor: Ahmed Ibrahim Mohamed Ibrahim, Khartoum (SD)

( * ) Notice: Subject to any disclaimer, the term of this patent is extended or adjusted under 35 U.S.C. 154(b) by 570 days.

(21) Appl. No.: 18/043,051

(22) PCT Filed: Sep. 1, 2021

(86) PCT No.: PCT/SD2021/000005
§ 371 (c)(1),
(2) Date: Feb. 27, 2023

(87) PCT Pub. No.: WO2022/098268
PCT Pub. Date: May 12, 2022

(65) Prior Publication Data
US 2024/0240186 A1 Jul. 18, 2024

(51) Int. Cl.
*C12N 15/113* (2010.01)
*A61P 31/18* (2006.01)
(52) U.S. Cl.
CPC .......... *C12N 15/1132* (2013.01); *A61P 31/18* (2018.01); *C12N 2310/11* (2013.01); *C12N 2310/315* (2013.01); *C12N 2310/322* (2013.01); *C12N 2310/3231* (2013.01)

(58) Field of Classification Search
CPC ............ C12N 15/1132; C12N 2310/11; C12N 2310/315; C12N 2310/322; C12N 2310/3231; A61K 31/712; A61P 31/18
See application file for complete search history.

(56) References Cited

FOREIGN PATENT DOCUMENTS

WO          9503407 A2    2/1995
WO      2005041874 A2    5/2005
WO   WO-2014186649 A2 * 11/2014   .......... C12N 15/113

OTHER PUBLICATIONS

Google AI Overview, downloaded from antisense to HIV don't work on other viruses—Google Search on Aug. 19, 2025.*
Google AI Overview, downloaded from will antisense to HIV-1 work on other HIV strains—Google Search on Aug. 19, 2025.*

* cited by examiner

*Primary Examiner* — Terra C Gibbs
(74) *Attorney, Agent, or Firm* — Bayramoglu Law Offices LLC

(57) ABSTRACT

Modified antisense mucleic acid molecules ending with or without chain terminating bases targeting the HIV-1 viral genomic RNA 3' LTR region, and uses thereof for inhibiting HIV-1 replication and infection, are disclosed. The antisense mucleic acid molecules more specifically target a sequence corresponding to about nucleotide 9628 to about nucleotide 9642 of HIV-1 clone pNL4-3.

12 Claims, 5 Drawing Sheets

Specification includes a Sequence Listing.

SEQUENCE LISTING

```
<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: This sequence is synthetized.
<220> FEATURE:
<221> NAME/KEY: modified_base
<222> LOCATION: (2)..(2)
<223> OTHER INFORMATION: phosphorothioate modified
<220> FEATURE:
<221> NAME/KEY: modified_base
<222> LOCATION: (2)..(2)
<223> OTHER INFORMATION: 2'-fluoro modified
<220> FEATURE:
<221> NAME/KEY: modified_base
<222> LOCATION: (3)..(3)
<223> OTHER INFORMATION: phosphorothioate modified
<220> FEATURE:
<221> NAME/KEY: modified_base
<222> LOCATION: (5)..(5)
<223> OTHER INFORMATION: phosphorothioate modified
<220> FEATURE:
<221> NAME/KEY: modified_base
<222> LOCATION: (6)..(6)
<223> OTHER INFORMATION: 2'-fluoro modified
<220> FEATURE:
<221> NAME/KEY: modified_base
<222> LOCATION: (7)..(7)
<223> OTHER INFORMATION: phosphorothioate modified
<220> FEATURE:
<221> NAME/KEY: modified_base
<222> LOCATION: (8)..(8)
<223> OTHER INFORMATION: 2'-fluoro modified
<220> FEATURE:
<221> NAME/KEY: modified_base
<222> LOCATION: (9)..(9)
<223> OTHER INFORMATION: phosphorothioate modified
<220> FEATURE:
<221> NAME/KEY: modified_base
<222> LOCATION: (10)..(10)
<223> OTHER INFORMATION: 2'-fluoro modified
<220> FEATURE:
```

```
<221> NAME/KEY: modified_base
<222> LOCATION: (11)..(11)
<223> OTHER INFORMATION: phosphorothioate modified
<220> FEATURE:
<221> NAME/KEY: modified_base
<222> LOCATION: (13)..(13)
<223> OTHER INFORMATION: phosphorothioate modified
<220> FEATURE:
<221> NAME/KEY: modified_base
<222> LOCATION: (14)..(14)
<223> OTHER INFORMATION: bridged adenosine modified
<220> FEATURE:
<221> NAME/KEY: modified_base
<222> LOCATION: (14)..(14)
<223> OTHER INFORMATION: phosphorothioate modified

<400> SEQUENCE: 1
acgggcacac actac                                                      15

<210> SEQ ID NO 2
<211> LENGTH: 15
<212> TYPE: DNA
<213> ORGANISM: Artificial Sequence
<220> FEATURE:
<223> OTHER INFORMATION: This sequence is synthetized.
<220> FEATURE:
<221> NAME/KEY: modified_base
<222> LOCATION: (2)..(2)
<223> OTHER INFORMATION: phosphorothioate modified
<220> FEATURE:
<221> NAME/KEY: modified_base
<222> LOCATION: (2)..(2)
<223> OTHER INFORMATION: 2'-fluoro modified
<220> FEATURE:
<221> NAME/KEY: modified_base
<222> LOCATION: (3)..(3)
<223> OTHER INFORMATION: phosphorothioate modified
<220> FEATURE:
<221> NAME/KEY: modified_base
<222> LOCATION: (5)..(5)
<223> OTHER INFORMATION: phosphorothioate modified
<220> FEATURE:
<221> NAME/KEY: modified_base
<222> LOCATION: (6)..(6)
<223> OTHER INFORMATION: 2'-fluoro modified
<220> FEATURE:
<221> NAME/KEY: modified_base
<222> LOCATION: (7)..(7)
<223> OTHER INFORMATION: phosphorothioate modified
<220> FEATURE:
<221> NAME/KEY: modified_base
<222> LOCATION: (8)..(8)
<223> OTHER INFORMATION: 2'-fluoro modified
<220> FEATURE:
<221> NAME/KEY: modified_base
<222> LOCATION: (9)..(9)
<223> OTHER INFORMATION: phosphorothioate modified
<220> FEATURE:
<221> NAME/KEY: modified_base
<222> LOCATION: (10)..(10)
<223> OTHER INFORMATION: 2'-fluoro modified
<220> FEATURE:
<221> NAME/KEY: modified_base
<222> LOCATION: (11)..(11)
<223> OTHER INFORMATION: phosphorothioate modified
<220> FEATURE:
<221> NAME/KEY: modified_base
<222> LOCATION: (13)..(13)
<223> OTHER INFORMATION: phosphorothioate modified
<220> FEATURE:
<221> NAME/KEY: modified_base
<222> LOCATION: (14)..(14)
<223> OTHER INFORMATION: phosphorothioate modified
<220> FEATURE:
<221> NAME/KEY: modified_base
<222> LOCATION: (14)..(14)
<223> OTHER INFORMATION: bridged adenosine modified
```

-continued

```
<220> FEATURE:
<221> NAME/KEY: modified_base
<222> LOCATION: (15)..(15)
<223> OTHER INFORMATION: phosphorothioate modified
<220> FEATURE:
<221> NAME/KEY: modified_base
<222> LOCATION: (15)..(15)
<223> OTHER INFORMATION: dideoxy modified

<400> SEQUENCE: 2
acgggcacac actac                                                                      15

<210> SEQ ID NO 3
<211> LENGTH: 15
<212> TYPE: DNA
<213> ORGANISM: Artificial Sequence
<220> FEATURE:
<223> OTHER INFORMATION: This sequence is synthetized.
<220> FEATURE:
<221> NAME/KEY: modified_base
<222> LOCATION: (2)..(2)
<223> OTHER INFORMATION: phosphorothioate modified
<220> FEATURE:
<221> NAME/KEY: modified_base
<222> LOCATION: (3)..(3)
<223> OTHER INFORMATION: phosphorothioate modified
<220> FEATURE:
<221> NAME/KEY: modified_base
<222> LOCATION: (3)..(3)
<223> OTHER INFORMATION: 2'-fluoro modified
<220> FEATURE:
<221> NAME/KEY: modified_base
<222> LOCATION: (5)..(5)
<223> OTHER INFORMATION: phosphorothioate modified
<220> FEATURE:
<221> NAME/KEY: modified_base
<222> LOCATION: (5)..(5)
<223> OTHER INFORMATION: 2'-fluoro modified
<220> FEATURE:
<221> NAME/KEY: modified_base
<222> LOCATION: (7)..(7)
<223> OTHER INFORMATION: phosphorothioate modified
<220> FEATURE:
<221> NAME/KEY: modified_base
<222> LOCATION: (8)..(8)
<223> OTHER INFORMATION: bridged adenosine modified
<220> FEATURE:
<221> NAME/KEY: modified_base
<222> LOCATION: (9)..(9)
<223> OTHER INFORMATION: phosphorothioate modified
<220> FEATURE:
<221> NAME/KEY: modified_base
<222> LOCATION: (9)..(9)
<223> OTHER INFORMATION: 2'-fluoro modified
<220> FEATURE:
<221> NAME/KEY: modified_base
<222> LOCATION: (11)..(11)
<223> OTHER INFORMATION: phosphorothioate modified
<220> FEATURE:
<221> NAME/KEY: modified_base
<222> LOCATION: (11)..(11)
<223> OTHER INFORMATION: 2'-fluoro modified
<220> FEATURE:
<221> NAME/KEY: modified_base
<222> LOCATION: (13)..(13)
<223> OTHER INFORMATION: phosphorothioate modified
<220> FEATURE:
<221> NAME/KEY: modified_base
<222> LOCATION: (14)..(14)
<223> OTHER INFORMATION: phosphorothioate modified
<220> FEATURE:
<221> NAME/KEY: modified_base
<222> LOCATION: (15)..(15)
<223> OTHER INFORMATION: phosphorothioate modified

<400> SEQUENCE: 3
```

```
ggcacgcaca caact                                                          15

<210> SEQ ID NO 4
<211> LENGTH: 1639
<212> TYPE: DNA
<213> ORGANISM: Human immunodeficiency virus type 1
<220> FEATURE:
<221> NAME/KEY: LTR
<222> LOCATION: (1)..(1639)
<223> OTHER INFORMATION: strong promoter region

<400> SEQUENCE: 4
atcggtaccg ccacctggaa gggctaattt ggtcccaaaa aagacaagag atccttgatc     60
tgtggatcta ccacacacaa ggctacttcc ctgattggca gaactactag ccatggcggt    120
ggaccttccc gattaaacca gggttttttc tgttctctag gaactagaca cctagatggt    180
gtgtgttccg atgaagggac taaccgtctt gatgacacca gggccaggga tcagatatcc    240
actgaccttt ggatggtgct tcaagttagt accagttgaa ccagagcaag tagaagaggc    300
caaataagga gagaagaaca gtgtggtccc ggtccctagt ctataggtga ctggaaacct    360
accacgaagt tcaatcatgg tcaacttggt ctcgttcatc ttctccggtt tattcctctc    420
ttcttgtcct tgttacaccc tatgagccag catgggatgg aggacccgga gggagaagta    480
ttagtgtgga agtttgacag cctcctagca tttcgtcaca tggcccgaga gctgcgaaca    540
atgtgggata ctcggtcgta ccctacctcc tgggcctccc tcttcataat cacaccttca    600
aactgtcgga ggatcgtaaa gcagtgtacc gggctctcga cgatccggag tactacaaag    660
actgctgaca tcgagctttc tacaagggac tttccgctgg ggactttcca gggaggtgtg    720
gcctgggcgg gactggggag tggcgagcct aggcctcatg atgtttctga cgactgtagc    780
tcgaaagatg ttccctgaaa ggcgacccct gaaaggtccc tccacaccgg acccgccctg    840
acccctcacc gctcggctca gatgctacat ataagcagct gcttttttgcc tgtactgggt    900 ctctctggtt agaccagatc tgagcctggg agctctctgg gctaactagg gaacccactg    960
cttagagtct acgatgtata ttcgtcgacg aaaaacggac atgacccaga gaccaatctg   1020
gtctagactc ggaccctcga gagaccgatt gatcccttgg gtgacgaata gcctcaataa   1080
agcttgcctt gagtgctcaa agtagtgtgt gcccgtctgt tgtgtgactc tggtaactag   1140
agatccctca gacccttttta gtcagtgtgg aaaatctcgg agttatttcg aacggaactc   1200
acgagtttca tcacacacgg gcagacaaca cactgagacc attgatctct agggagtctg   1260
ggaaaatcag tcacaccttt tagtctagca gtggcgcccg aacagggact agtaaagcca   1320
gaggagatct ctcgacgcag gactcggctt gctgaagcgc gcacggcaag aggcgagggg   1380
agatcgtcac cgcgggcttg tccctgaact ttcgctttca tttcggtctc tctagagag    1440 ctgcgtcctg agccgaacga cttcgcgcgt gccgttctcc gctcccccgg cgactggtga   1500
gtacgccaaa aattttgact agcggaggct agaaggagag agatgggtgc gaggcggccg   1560
caagccgctg accactcatg cggtttttaa aactgatcgc ctccgatctt cctctctcta   1620
cccacgctcc gccggcgtt                                                1639

<210> SEQ ID NO 5
<211> LENGTH: 32
<212> TYPE: DNA
<213> ORGANISM: Artificial Sequence
<220> FEATURE:
<223> OTHER INFORMATION: This sequence is synthetized.

<400> SEQUENCE: 5
```

-continued

```
atcggtaccg ccacctggaa gggctaattt gg                                    32

<210> SEQ ID NO 6
<211> LENGTH: 29
<212> TYPE: DNA
<213> ORGANISM: Artificial Sequence
<220> FEATURE:
<223> OTHER INFORMATION: This sequence is synthetized.

<400> SEQUENCE: 6
ttgcggccgc ctcgcaccca tctctctcc                                        29
```

COMB SHAPED ANTIVIRALS ENDING WITH OR WITHOUT CHAIN TERMINATING BASES

CROSS REFERENCE TO THE RELATED APPLICATIONS

This application is the national phase entry of International Application No. PCT/SD2021/000005, filed on Sep. 1, 2021, which is based upon and claims priority to Sudan Patent Application No. 5440/2021, filed on Nov. 4, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBELD001_Sequence Listing-20231114-LS_ST25.txt, created on 11/21/2023, and is 7,059 bytes in size.

TECHNICAL FIELD

The present disclosure relates to the technical field of biological medicine, and particularly to comb shaped antivirals ending with or without chain terminating bases.

BACKGROUND

The first therapy to work against HIV was the nucleoside reverse transcriptase inhibitor zidovudine which was approved by the FDA in 1987. By 1996, research showed the advantages of combining medicines to treat HIV, and using this type of treatment is called anti-retroviral therapy which is recommended by the department of health and human services (DHHS) and the world health organization (WHO).

Generally drugs used to treat HIV infection are organized into five classes based on the stage of the HIV life cycle they inhibit. As of 2019, there are at least 28 individual agents (called drug molecules) and at least 13 fixed dosed combination (FDC) drugs comprised of two or more molecules targeting the viral proteins reverse transcriptase (RT), protease and integrase, as well as the cellular entry co-receptor CCR5.

Thirteen of the above mentioned anti-retroviral drugs target the viral protein reverse transcriptase, these drugs belong to one of two different categories, the nucleoside or nucleotide reverse-transcriptase inhibitors (NRTIs) category which lack 3' hydroxyl group on their ribose or ribose mimic moiety and include drugs such as Emtricitabine (2',3'-dideoxy-5-fluoro-3'-thiacytidine), Lamivudine, Abacavir, di-adenosine, stavudine, zidovudine and Zalcitabine which has been discontinued because of its inconvenient three-times daily frequency, its low potency and the associated serious adverse events4,5. The second category is the non-nucleoside or nucleotide reverse-transcriptase inhibitors (NNRTIs) which bind into a hydrophobic pocket close to the polymerase active site and inhibit the chemical step of polymerization reaction, drugs include rilpivirine, etravirine, delavirdine, doravirine, efavirenz and nevirapine.

It is worth to mention that none of the anti-HIV drugs is able to eliminate the virus completely and all these drugs are associated with a number of short- and long-term side effects.

Despite advances in treatment, finding a cure for HIV remains a top priority. Chronic HIV infection is associated with increased risk comorbidities, such as diabetes and cardiovascular disease. Additionally, people with HIV must remain adherent to daily antiretroviral therapy, because lapses in medication adherence can lead to viral rebound and disease progression.

Also the HIV virus is able to develop rapidly mutations that enable it to resist nearly all of these drugs. Mutations that affect the HIV virus susceptibility to treatment are listed in FIGS. 1-4.

For decades researchers have studied the possibility to use nucleic acids as afrti fral? therapeutics. In theory compounds such as antisense oligonucleotides, ribozymes', DNAymes, and aptamers can be designed to trigger the sequence specific inhibition of particular mRNA transcripts including the viral genomes. However difficulties with their efficiency, off-target effects, toxicity, delivery and stability halted the development of nucleic acid based therapeutics that can be used in the clinic.

GEM 91 (gene expression modulator) is a 25-mer oligonucleotide phosphorothioate complementary to the gag initiation site of HIV-1 was shown to have multiple inhibitory mechanisms. Non sequence-dependent inhibition of virus entry and reverse transcription were shown to play a predominant role in the total antiviral activity due to a polyanionic effect of the phosphorothioate backbone, similar to dextran sulphate. The intracellular RNase H cleavage by GEM 91 is at best inefficient since the free uptake of GEM 91 was almost exclusively restricted to endosomal vesicles within the cytosol.

Hybridon developed GEM-92, a second generation oral phosphorothioate gapmer directed against the gag gene in HIV-1 mRNA, as a potential treatment for HIV-1 infection. Such second-generation oligonucleotides maintain the ability to induce RNA cleavage by RNase H, yet are more greatly protected against degradation by serum and cellular nucleases, and also have higher RNA binding. However, no second generation and only a single first generation antisense oligonucleotide (fomiversin), for the treatment of CMV-induced retinitis in AIDS patients, have been clinically approved.

Small RNAs are now a growing class of molecules with the potential to complement or replace current therapies. They are being evaluated for use in ex vivo gene therapy and with advances that have been made in their systemic delivery, may soon be evaluated for use in combination drug therapy. Examples of these RNAs are many including the small activating RNAs which are double stranded RNAs able to activate gene expression. The short hairpin RNAs that use RNA interference pathway, RNA decoys and aptamers those bind specifically to a protein or RNA as well as ribozymes that mediate cleavage.

Ribozymes first clinical study to target a disease was conducted in HIV positive patients in 1996. Hairpin ribozymes were developed to target HIV U5 and pol and contain the stem loop II sequence of HIV-Rev, thus serving as both a ribozyme and a RNA decoy.

In spite of all these efforts new candidates for development as potential drugs or virucides against HIV-1 infection and AIDS continue to be needed.

Using new designs that add the advantages of both small molecules more certainly the nucleotide reverse transcriptase inhibitors to the advantages of small RNAs or DNA antisense compounds or their analogs as in our design may help to overcome many resistance associated problems and may even allow eradicating the virus.

SUMMARY

The present invention provides methods for designing antiviral modified single stranded antisense nucleotides. As they are composed of a number of oligonucleotides and they are linear in shape we imagined that they will resemble the comb shape. These combs were tested against the HIV-1. They were able to align to the 3' LTR region of the HIV-1 PNL4-3 strain and directly cut the genomic RNA using viral reverse transcriptase by making a fatal nick in both of the HIV genomic RNA strands difficult to be repaired inhibiting the virus the cDNA synthesis.

DETAILED DESCRIPTION OF THE EMBODIMENTS

To prove the activity of such compounds we have used a colorimetric (Roche)cell free HIV reverse transcriptase assay which takes advantage of the ability of reverse transcriptase (RT) to synthesize DNA starting from a viral template.

Figure 1:
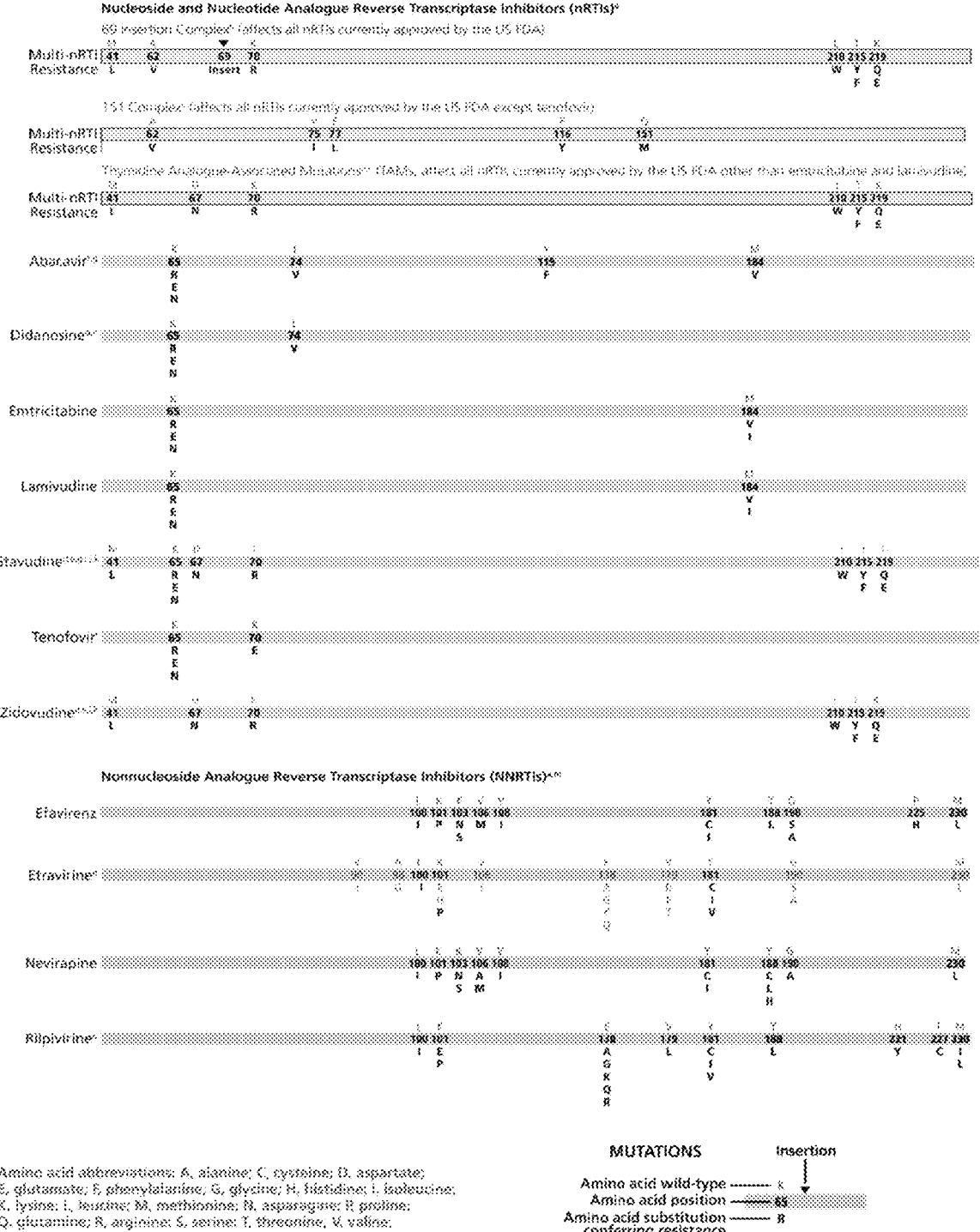
FIG. 1. Mutations in the reverse transcriptase gene associated with resistance to reverse transcriptase inhibitors.
Figures 2, 3:
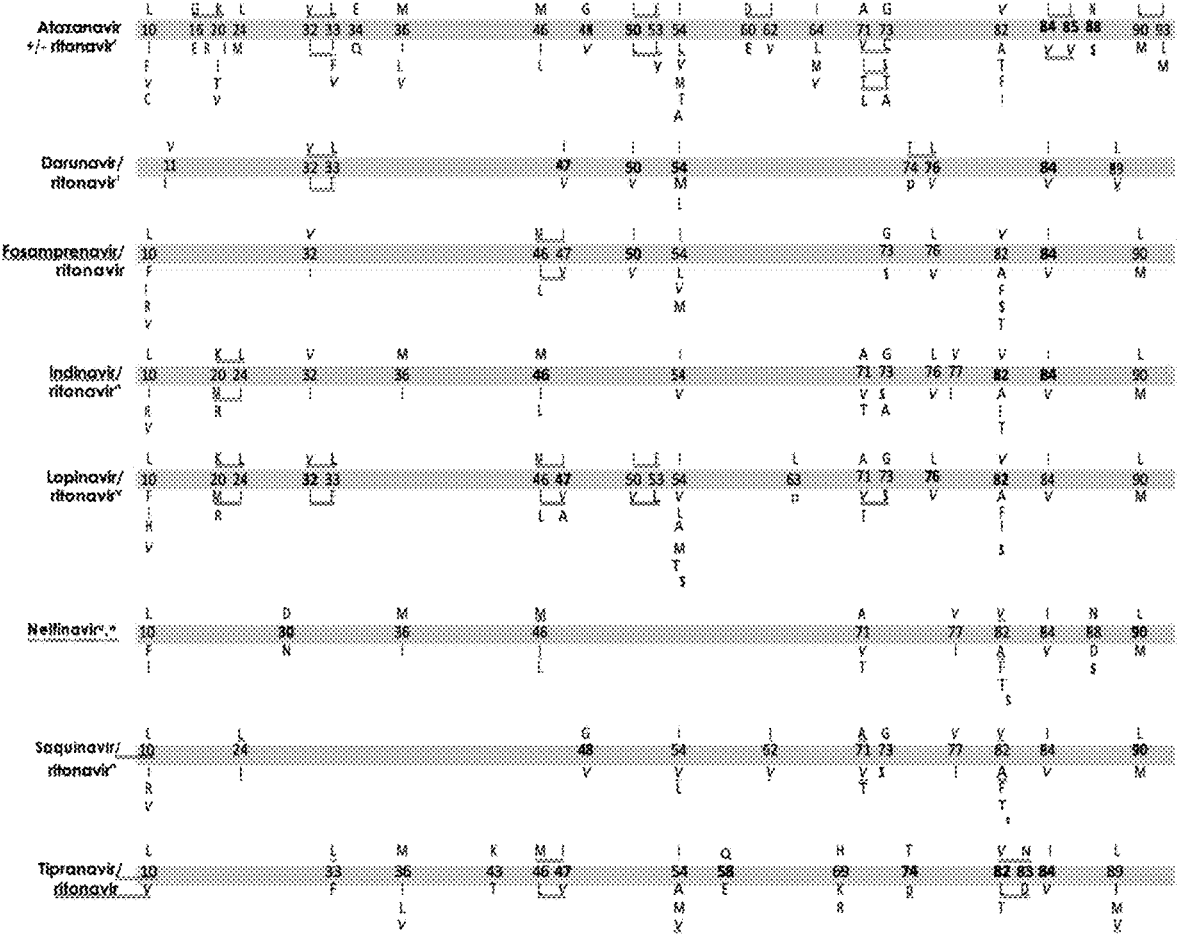
FIG. 2. Mutations in the protease gene associated with resistance to protease inhibitors.
FIG. 3. Mutations in the envelope gene associated with resistance to entry inhibitors.
Figure 4:
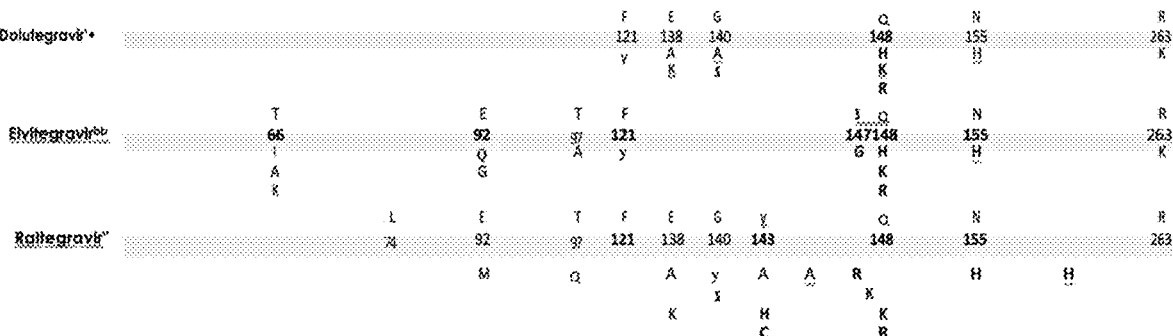
FIG. 4. Mutations in the integrase gene associated with resistance to integrase strand transfer inhibitors.
Figure 5:
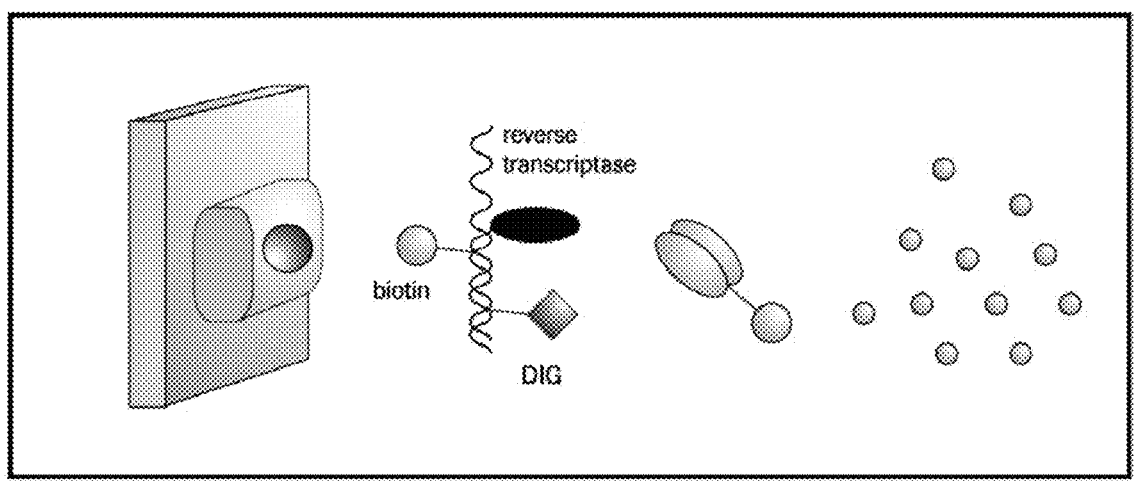
FIG. 5. The cell-free HIV-RT assay test principle.

Digoxigenin- and biotin-labeled nucleotides were incorporated into the RT-synthesized DNA molecule. Then, the detection and quantification of synthesized DNA (as a parameter for RT activity) was done using a sandwich ELISA protocol: Biotin-labeled DNA binds to the surface of micro-plate (MP) modules that have been precoated with streptavidin. In the next step, an antibody to digoxigenin conjugated to peroxidase (anti-DlG-POD) binds to the digoxigenin-labeled DNA. In the final step, the peroxidase substrate ABTS was added. The peroxidase enzyme catalyzes the cleavage of the substrate, producing a colored reaction product. The intensity of the color product was then determined using an ELISA reader and is directly correlated to the level of RT activity in the sample (FIG. 5).

Our antisense compounds (combs) have been directed against a sequence corresponding to about nucleotide 9628 to about nucleotide 9642 of HIV-1 clone pNL4-3 (GenBank accession No. Ml 9921.2), Nucleotide numbering described herein uses numbering in the reference HIV-1 clone pNL4-3 (GenBank accession No. M19921.2).

The corresponding positions/sequences (which defines the region targeted by the present invention antisense nucleic acid molecules) in any HIV-1 strain may be easily identified, It will be understood that the corresponding sequences in other HIV-1 strains may not be identical to the corresponding sequence of HIV-1 clone pNL4-3 consequently the antisense nucleic acid molecule sequence may be adapted.

We have synthesized two modified antisense oligonucleotides overlapping the strong promoter region of HIV-1. Compounds were only different in the last 3' base which was modified in the second compound to ddC instead of cytidine, compound 1 sequence was 5'-A*fC*GG* GfC*AfC*AfC*AC*T*+A*C-3 (SEQ ID NO: 1), while compound 2' sequence was 5'-A*fC* GG*GfC*AfC* AfC*AC*T*+A*ddC-3 (SEQ ID NO: 2), where: +N (eg: +A, +C, +G and +T) represents BNA; *represents phosphorothioate; fN represents 2'-fluoro RNA; eN represents 2'-0 methoxy ethyl.

We have also synthesized a scrambled control with the sequence 5'-G*G*fCA*3*C+A*fCA*fCA*A *C*T-3' (SEQ ID NO: 3) Azidothymidine was used as a positive control.

The above mentioned modifications as we believe will produce stable compounds against the HIV reverse transciptase RNase H as well as cellular nucleases; they can also improve the antisense activity.

Figure 6:
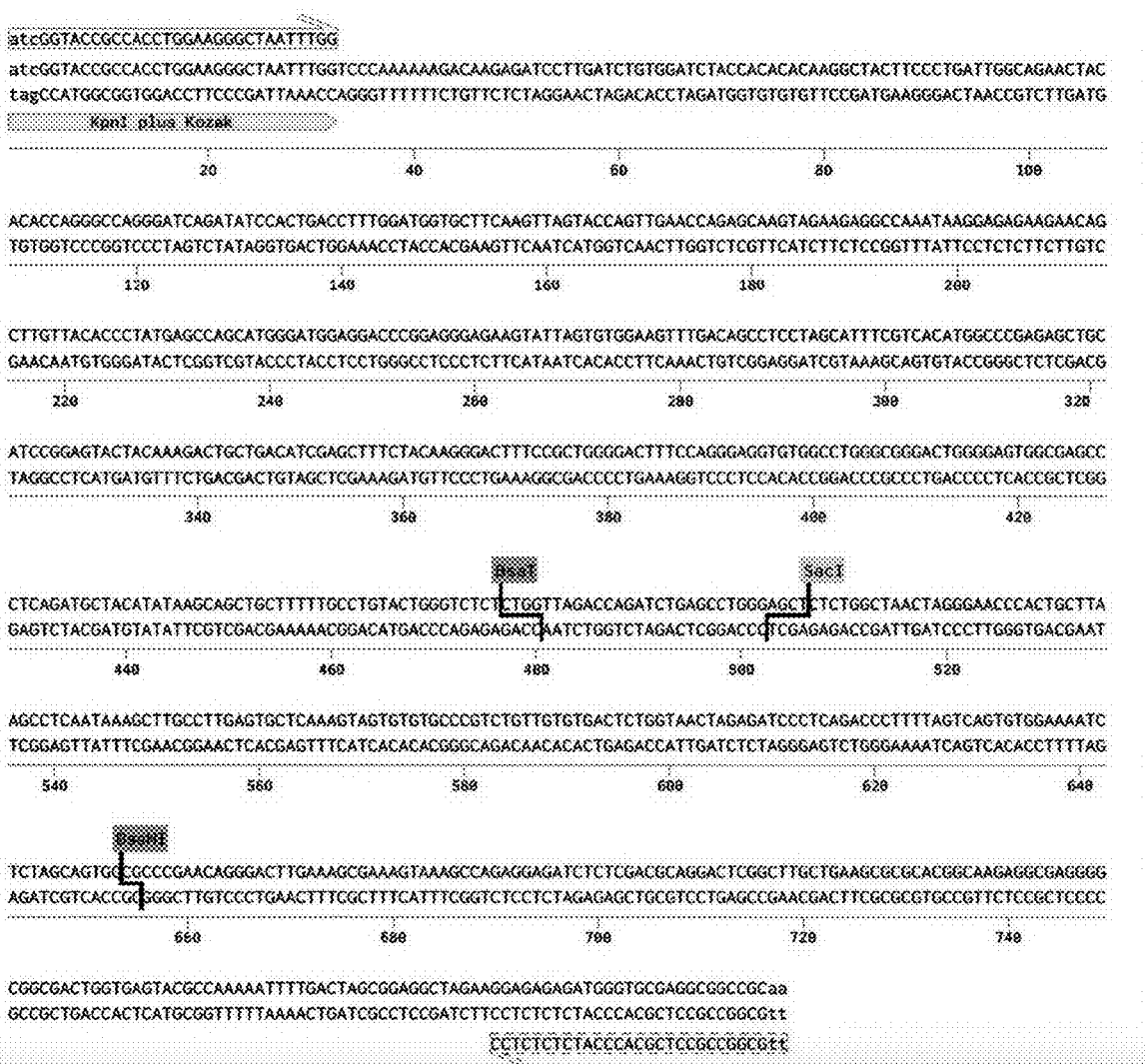
FIG. 6. Cloning of the HIV-1 strong promoter region (SEQ ID NO. 4).

The strong promoter region of HV-1 (SEQ ID NO: 4) was obtained by PCR amplification and cloned into pcDNA3.1DNA using primers:

```
                                    (SEQ ID NO: 5)
 5'-ATCGGTACCGCCACCTGGAAGGGCTAATTTGG-3'
 and (SEQ ID NO: 6)
 5' TTGCGGCCGCCTCGCACCCATCTCTCTCC-3'
 (FIG. 6).
```

After PCR amplification, the DNA was purified using the Qiaquick PCR purification kit (Qiagen). The purified PCR product was then digested using restriction enzymes Kpnl and Notl, and cloned into a linearized pcDNA3.1 vector (prepared using Kpnl and Notl) using standard cloning techniques and DH5a competent cells. The resulting construct was confirmed by the colony PCR technique and DNA sequencing. Single bacterial colonies carrying the HIV-1-promoter-pcDNA3.1 vector were used to initiate an overnight liquid culture to amplify the plasmid. The plasmid DNA was isolated and purified using Qiagen Maxi-Prep kit.

The plasmid (HIV-1-promo ter-pcDN A3.1) was first linearized using Xhol (NEB), then purified by phenol/chloroform extraction and ethanol precipitation. The linearized plasmid was dissolved in nuclease-free water. The mMESSAGEmIACHINE T7 Ultra transcription kit (Invitrogen), was used to generate the replicon RNAs in the correct orientation from the linearized vector according to manufacturer's instruction.

Briefly, 100 pL of T7 transcription reaction, containing 1 μg of linearized vector and 15 pL of extra GTP, was incubated at 37° C. for 2.5 h to increase the length of the transcripts. After incubation, 5 pL of TURBO DNase was added and the reaction was incubated at 37° C. for 15 min to digest DNA. Polyadenylation of the in vitro transcribed RNA was done using the Poly (A) Tailing Kit (ThermoFisher). The synthesized RNA ■ was purified by phenol: chloroform extraction and isopropanol precipitation.

The above mentioned antisense compounds were then briefly centrifuged and resuspended in non-DEPC-treated water at a concentration of 1 mM.

As previously mentioned, to quantify the inhibitory effect of the test oligonucleotides against HV-1 RT, we used the Reverse Transcriptase Assay, Colorimetric kit (HIV RT assay kit, Roche USA Cat. No. 11 468 120 910), following the manufacturer's instructions.

Recombinant HIV-1 RT (4 ng) was diluted in lysis buffer (Tris-buffer: 50 mMTris, 80 mM potassium chloride, 2.5 mM DTT, 0.75 mM EDTA and 0.5% Triton X-100, pH 7.8) in a reaction tube. dATP, dGTP, and dCTP (30 µM) were added to 1 ml of incubation buffer together with the kit provided vial-3 [containing Tris-HCl (50 mM, pH 7.8), DIG-dUTP, biotin-dUTP, and dTTP], Template RNA (1 µg) and 10 µM of OligodT (reaction mixture) were then added. This is termed 'the reaction mixture'.

Next, we added the test antisense oligos at three concentrations (0.5, 5 &50 µM) to the reaction mixture and incubated for 1 h at 37° C. We also incubated the reaction mixture without any oligos, as our no-inhibitor control. Reaction mixture plus oligos with no HIV1-RT was used as negative controls. These samples were then transferred to wells of the kit's Micro Plate module. The plate was covered and incubated for 1 h at 37° C. The plates were then washed five times with wash buffer. Anti-DIG-POD (200 µl working dilution) was added and incubated for 1 h at 37° C. The plates were again washed five times with wash buffer. ABTS substrate solution (200 µl) was added and incubated at room temperature for 30 min until a green color developed. The plate was then read at 405 nm in an ELISA reader. Lysis buffer without RT was used as a negative control and azidothymidine (0.5 mM AZT) with RT was used as a positive control.

The resulting colorimetric signal intensity is directly proportional to the RT activity. Therefore, the inhibitory activity of the tested RT inhibitors can be expressed as the percent inhibition relative to a sample without inhibitor.

Figure 7:
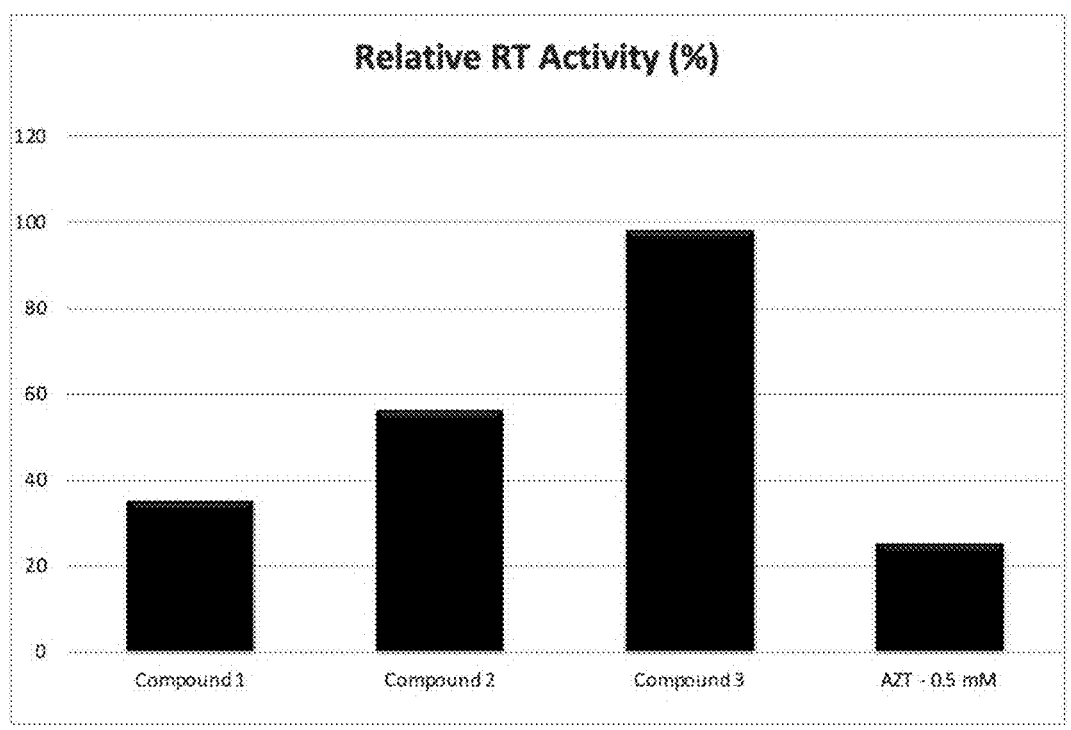
FIG. 7. Relative RT activities (%) of HIV-RT when treated with Oligos #1-6 at concentrations of 0.5, 5, and 50 uM.
Figure 8:
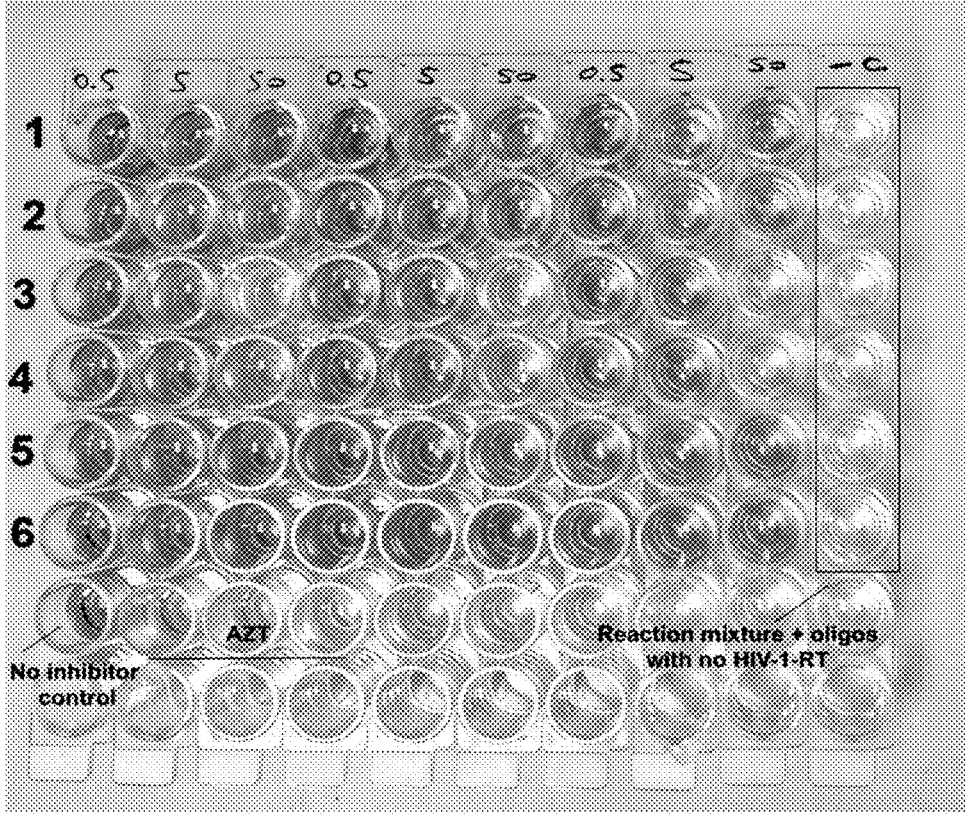
FIG. 8. Developed micro plate modules showing the RT activities, A stronger color corresponds to greater RT activity.

Both of compounds 1 & 2 (Compounds 3 and 4 in the microtiter plate) did inhibit HIV-RT activity (35±1.72% and 56±40.58% activities at 50 µM relative to the no-inhibitor control, respectively). As expected, the scrambled antisense compound (Compound 6 in the microtiter plate) did not inhibit HIV-RT activity (98±0.70% activities at 50 µM relative to the no-inhibitor control, respectively). Data are shown in FIGS. 7 and 8.

The positive control azidothymidine (AZT, 0.5 mM) reduced HIV-RT activity to 25±1.68% relative to the no-inhibitor control.

We can conclude that under the conditions tested, both of the comb shaped antisense compounds can inhibit the RT activity of the HIV-RT, with percentage reductions of 65% and 44%, respectively, when used at a 50 µM concentration.

Although the present invention has been described hereinabove, it can be modified, without departing from the spirit and nature of the subject invention as defined in the appended claims.

What is claimed is:

1. Antisense nucleic acid molecules directed against a sequence corresponding to nucleotide 9628 to nucleotide 9642 of HIV-1 clone pNL4-3 ending with or without a 3' terminal ddC and comprising one of the following sequences (I) or (II):

(I) 5'-A*fC*GG*GfC*AfC*AfC*AC*T*+A*C-3' (SEQ ID NO: 1)

(II) 5'-A*fC*GG*GfC*AfC*AfC*AC*T*+A*[ddC]-3' (SEQ ID NO: 2);

wherein "+N" denotes a bridged nucleic acid nucleotide wherein "N" is "A," "C," "G" or "T", "*" denotes a phosphorothioate linkage, "fN" denotes a 2'-fluoro ribonucleotide, and "[ddC]" denotes a 2',3'-dideoxycytidine at the 3' terminus.

2. A pharmaceutical composition comprising the antisense nucleic acid molecules of claim 1, an excipient, and/or a cell delivery agent.

3. The pharmaceutical composition of claim 2, wherein the antisense nucleic acid molecule is SEQ ID NO: 1.

4. The pharmaceutical composition of claim 2, wherein the antisense nucleic acid molecule is SEQ ID NO: 2.

5. A method of designing an antisense oligomer to target HIV-1 genomic RNA, comprising (i) identifying, in an HIV-1 strain, the sequence corresponding to nucleotides 9628-9642 of HIV-1 clone pNL4-3; and (ii) adapting the sequence of an antisense nucleic acid molecule according to claim 1, wherein the molecule has a chain-terminating base at the 3' end, to be complementary to the identified sequence.

6. A method of using the antisense nucleic acid molecules of claim 1, comprising administering to a subject in need thereof an effective amount of the antisense nucleic acid molecule of claim 1, wherein the molecule hybridizes to an accessible sequence at a 3' or 5' LTR region of the HIV-1 clone pNL4-3.

7. A method of treating HIV-1 infection using the antisense nucleic acid molecule of claim 1, comprising administering to a subject in need thereof a therapeutically effective amount of the molecule.

8. A method for treating an HIV-1 infection in a subject, comprising administering to the subject an effective amount of (a) the antisense nucleic acid molecule of claim 1 or (b) a pharmaceutical composition comprising the antisense nucleic acid molecule and an excipient, and/or a cell delivery agent.

9. The method of claim 8, wherein the antisense nucleic acid molecule comprises a 3' chain-terminating ddC.

10. The method of claim 8, wherein the antisense nucleic acid molecule is SEQ ID NO: 1.

11. The method of claim 8, wherein the antisense nucleic acid molecule is SEQ ID NO: 2.

12. The method of claim 8, wherein the pharmaceutical composition comprises the antisense nucleic acid molecule SEQ ID NO: 2, an excipient, and a cell delivery agent.

* * * * *